United States Patent [19]
Hashimoto

[11] Patent Number: 5,749,465
[45] Date of Patent: May 12, 1998

[54] CONTAINER

[75] Inventor: Kimio Hashimoto, Kunitachi, Japan

[73] Assignee: Kabushikigaisha Daiwa Riken Kogyo, Kunitachi, Japan

[21] Appl. No.: 635,935

[22] PCT Filed: Feb. 3, 1994

[86] PCT No.: PCT/JP94/00153

§ 371 Date: Mar. 21, 1996

§ 102(e) Date: Mar. 21, 1996

[87] PCT Pub. No.: WO95/21110

PCT Pub. Date: Aug. 10, 1995

[51] Int. Cl.[6] .................................. B65D 85/20
[52] U.S. Cl. .................. 206/361; 206/443; 206/815; 221/309
[58] Field of Search ................ 206/15.3, 361, 206/362, 371, 443, 804, 815; 221/307, 309, 310, 303

[56] References Cited

U.S. PATENT DOCUMENTS

| 371,621 | 10/1887 | Offrell | 221/309 |
|---|---|---|---|
| 1,414,946 | 5/1922 | Graham | 221/309 |
| 1,522,776 | 1/1925 | Glanzer | 221/309 |
| 4,289,249 | 9/1981 | Cripe | 206/371 |
| 4,664,291 | 5/1987 | Gunderson | |
| 4,989,730 | 2/1991 | Lemoine | 206/362 |
| 5,131,536 | 7/1992 | Wu | 206/362 |
| 5,579,910 | 12/1996 | Bennett | 206/362 |

FOREIGN PATENT DOCUMENTS

| 57-134045 | 8/1982 | Japan . |
|---|---|---|
| 64-7870 | 1/1989 | Japan . |
| 1-92877 | 6/1989 | Japan . |
| 3-126884 | 12/1991 | Japan . |

*Primary Examiner*—David T. Fidei
*Attorney, Agent, or Firm*—Morgan & Finnegan, L.L.P.

[57] ABSTRACT

A container accommodating a rodlike object (6) is comprising of a cylinder body (1), a shutter portion (2), and a cap (3). A retrieving port (10) for taking out the rodlike object 6 by holding the middle portion of the rodlike object 6 by fingers (7) and a through-hole for the head portion (11) for passing the head portion of the rodlike object are formed on the circumference wall of the cylinder body, in which a neck portion (12) having a clearance (12a) formed to have a smaller width than the thickness of the middle portion of the rodlike object is formed between the retrieving port and the through-hole for the head portion. The cylinder body is unitedly assembled thereon with the shutter portion and the cap in order, in which a shutter is opened by operating the rotation of the cap. According to the aforementioned structure, production of each part is easier, fewer numbers of parts, and further simplified assembly are possible, resulting in a small cost of production.

14 Claims, 16 Drawing Sheets

FIG. II

CONTAINER

TECHNICAL FIELD

This invention relates to a container in which a rodlike object, such as a cotton swob and a toothpick, can be hygienically used and easily taken out and, more particularly, to the container capable of improving operability when the rodlike object is taken out and assembly when the container is produced.

BACKGROUND ART

Conventionally, a rodlike object, such as a cotton swob and a toothpick, is accommodated in a capped container, in which the rodlike object is taken out after a cap is removed. Lately, cotton swob usage has tended to increase towards ordinary households and hospitals. The cotton swob is usually used as a daily medical instrument, but also the usage of the cotton swob is opened to other fields, for example, use as one part of a head cleaner for acoustic equipment and so on.

The cotton swob is accommodated in, for example, the capped container or a package bag having flexibility. The cotton swob accommodated in the capped container is taken out after the cap is removed when the cotton swob is required. And, the cotton swob accommodated in the package bag is taken out by being held by the stem portion of the cotton swob from an opening portion after the opening is formed by tearing along a perforated area formed to correspond with the stem portion of the cotton swob. As an example of this case, a cotton swob container according to Japanese Patent Application Laid-open No. Sho 58-19697 is that an inner cylinder area accommodating the cotton swob is fitted with in an external cylinder to be able to move in the vertical direction of the external cylinder, and the cotton swob is taken out from an opening formed on the inner cylinder which is lifted up in use.

In fact, the capped container can accommodate an abundance of rodlike objects, however, the cotton portion is placed in the side of an extracting opening, thereby it is difficult to be hygienically used, the cotton portion of the cotton swob can be touched by fingers or, at this time, the other cotton portions of the cotton swobs are touched. If a pair of tweezers are used for extracting the cotton swobs, the container should therefore include a pair of tweezers, resulting though in difficult manipulation.

Further, there are common disadvantages among various containers accommodating rodlike objects, such as a cotton swob and a toothpick, for example, if the container accidentally falls on the floor and the cap dislodges from the container, the cotton swobs are scattered on the floor, with the result that the cotton swobs cannot be used.

It is an object of the present invention to provide the container with improvements in the operability when a rodlike object is taken out and in the assembly of the cap, the shutter and the cylinder body of the container.

DISCLOSURE OF THE INVENTION

The present invention is structured so that a container, having an open topped cylinder body for accommodating a rodlike object and a cap for covering an opening in the cylinder body, has a retrieving port formed on a circumference wall of the open topped cylinder body to retrieve the rodlike object by holding the middle portion of the rodlike object, and a through-hole for a head portion of the rodlike object which is formed to link through a neck portion to the retrieving port, the width of the neck portion being formed to be smaller than the thickness of the middle portion of the rodlike object.

The other embodiments according to the present invention are characterized by including one or more of the following structures:

(1) The neck portion is structured with a non-clearance incision or a slot clearance.

(2) The open topped cylinder body has a divider dividing the inside of the open topped cylinder body into a number of rooms and moving therein to be relatively connected with the cap, so that the retrieving port corresponds to one room divided by the divider by turning the cap.

(3) The open topped cylinder body has the divider dividing the inside of the open topped cylinder body into a number of rooms and moving therein, and a shutter portion includes a shutter opening the retrieving port and the through-hole head portion which are formed to the open topped cylinder body, in which the shutter portion is rotated to be linked with the divider.

(4) In (3), the shutter portion has an engaging stop means with the corresponding number in response to the number of rooms divided by the divider for engaging between the shutter portion and the cap.

(5) In (2) and (3), the divider has a receiving plate receiving the lower end of the rodlike object accommodated in each room divided by the divider to place between the floor of the cylinder body and the divider.

(6) In (5), the divider and the receiving plate are unitedly formed.

(7) The floor of the cylinder body has a step at a border portion between a lower level on the floor in the area of the retrieving port and a stepped higher level on the floor in the area away from the retrieving port, the step causing the rodlike object to lean toward the retrieving port at the top end when the bottom end of the rodlike object stands against the step.

(8) The container has the shutter portion having an annular ring inserted between a shutter covering the retrieving port, the neck portion, and the through-hole for the head portion provided at the cylinder body and the upper portion of the cylinder body to be provided with an engagement means for engaging with the cap on an upper face of a thick portion formed in the annular ring, in which the shutter portion causes the annular ring to insert into the upper portion of the cylinder to cause the thick portion of the annular ring to abut an opening edge of the cylinder body to rotate, so that the retrieving port is opened by rotating the shutter portion by operating the rotation of the cap.

(9) In (8), the cap is provided with a fitting means provided on an inner face of the thick portion formed in the annular ring of the shutter portion or an upper inner face of the cap for fitting.

(10) In (8), the shutter portion has the annular ring formed in a double-wall structure inserted into the upper portion of the cylinder body, the annular ring being provided with a fitting means for fitting with the cap on the lower inner wall of the annular ring placed in the cylinder body.

(11) In (10), the engagement means for engaging with the cylinder body is provided on the inside of an outer wall of the annular ring separately placed on the outer area of the cylinder body and the fitting means for fitting with the cap is provided on the lower inner wall of the annular ring, the engagement means and the fitting means being provided on the same level line.

The present invention structured as above has the following effects.

In using the container, the cap is rotated to open the shutter, fingers hold the middle portion of the rodlike object being in the retrieving port, and the rodlike object can be taken out to forcibly open the neck portion when being moved toward the outside by corresponding the head of the rodlike object to the through-hole for the head portion. At this time, the fingers are constrained by the neck portion and naturally cannot move toward the through-hole to the head portion, so that the fingers do not touch the head portion of the rodlike object. When the accommodated rodlike objects become fewer and freely move in the container, the rodlike objects are slant, therefore, it is easy for the rodlike objects to be polluted or soiled whereby the head of the rodlike objects protrude from the through-hole for the head portion, however, by providing the neck portion between the retrieving port and the through-hole for the head portion, the degree of slant of the rodlike object is smaller, and it is difficult for the rodlike object to protrude.

The container, formed with the step on the floor of the cylinder body, can be restrained to a small degree from slanting the rodlike object by standing the rodlike object against the step even when the accommodated rodlike objects are fewer, resulting in an easy retrieval of the rodlike objects from the retrieving port.

If the container accidentally falls on the floor, the neck portion can hinder the rodlike object from sticking out from the shock caused by falling, and prevent the rodlike objects from scattering to be impossible to be used in view of hygiene, resulting in the improvement of safety.

The container, which is composed of three members: the cylinder body, the shutter portion, and the cap, has the ability to open the retrieving port for the rodlike object by operating only the rotation of the cap by assembling the cylinder body with the shutter portion and the cap in order. According to the aforementioned structure, it is possible to produce more easily each part, to have a fewer number of parts, and to have a simplified assembly, resulting in a small cost of production.

The cap is movably provided by the fitting means provided on the inner face of either the shutter portion or the cylinder body, whereby the rotation of the cap can be smoothly operated for a long time, resulting in the improvement of operability and reliability of the retrieval of the rodlike object.

The double-wall structure of the shutter portion, in which the fitting means formed on the inner wall and the engaging stop means formed on the outer wall are mutually provided at the same level line, can assign a molding die at the level line provided with the fitting means and the engaging stop means, whereby wearing out of the die is decreased and the durability of the die is increased, resulting in the lower cost of production.

BEST MODE FOR CARRYING OUT THE INVENTION

The present invention will be explained with reference to the attached drawings in more detail below. Incidentally, here, a cotton swob container accommodating a cotton swob as a rodlike object will be applied.

Figure 1:
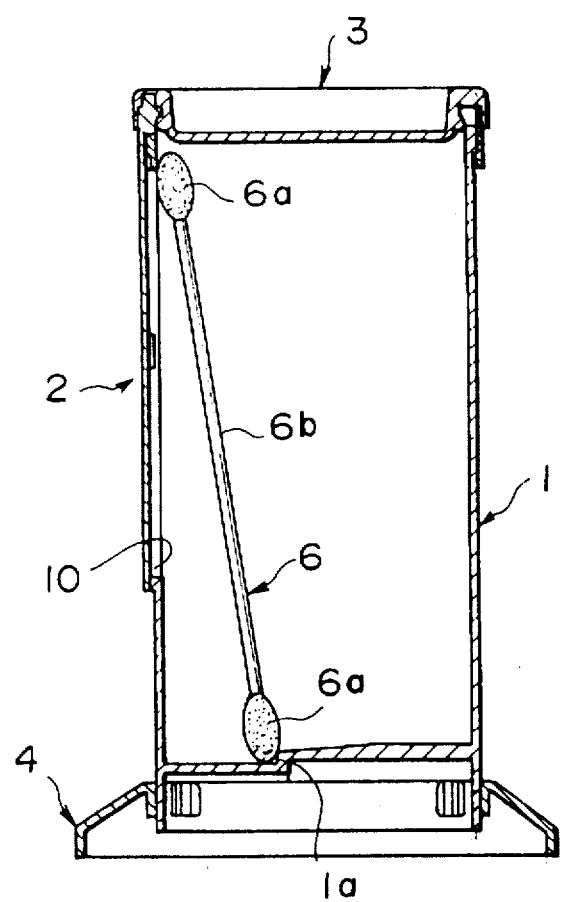
FIG. 1 is a sectional view of a cotton swob container of a first embodiment according to the present invention.
Figure 2:
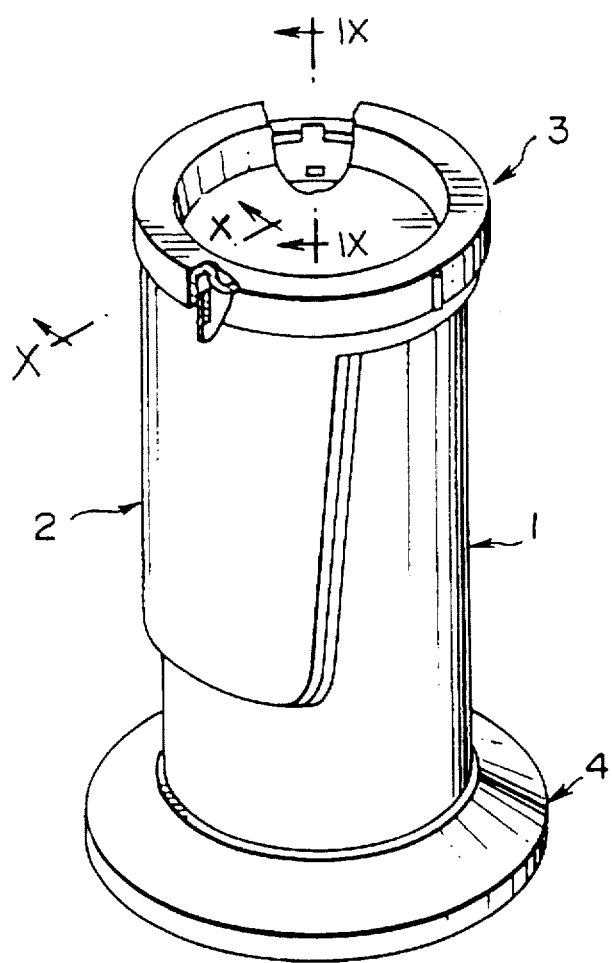
FIG. 2 is a perspective view of the cotton swob container of the first embodiment.

FIG. 1 shows a sectional structure of the cotton swob container of a first embodiment according to the present invention. FIG. 2 shows a visual structure of the cotton swob container of the first embodiment. The first embodiment is that a shutter portion is rotatably provided with a cylinder portion, in which the shutter portion is detachably joined to a cap body.

The cotton swob container is composed, as primary members, of a open topped cylinder body 1 accommodating a cotton swob 6 and having a retrieving cotton swob port 10 on its cylinder wall, a shutter portion 2 opening the retrieving cotton swob port 10 formed on the cylinder body, a cap 3 for closing the top end that opens of the cylinder body, and a pedestal 4 for affording stability to the cylinder body 1. The pedestal 4 is detachably provided to the cylinder body 1 to be attached to the cylinder portion if necessary.

Figure 3:
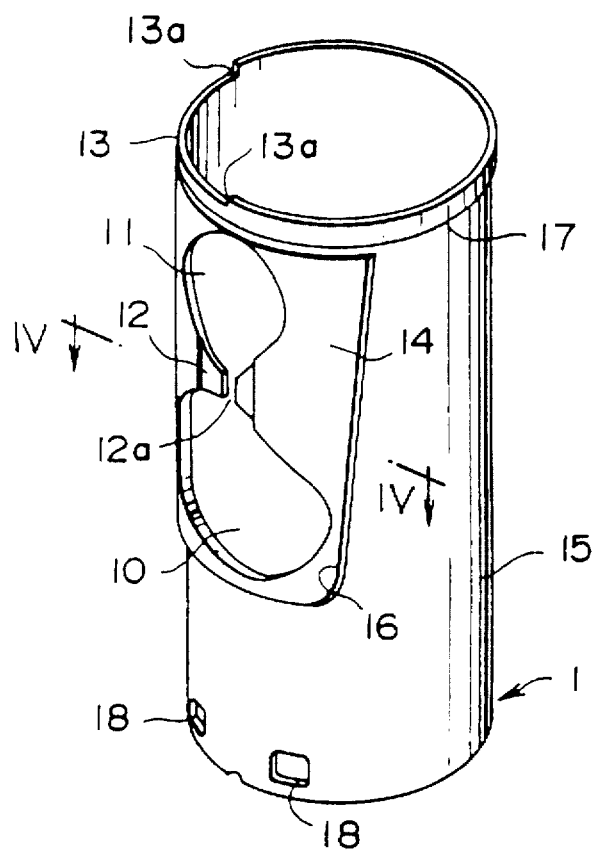
FIG. 3 is a perspective view of a cylinder body.

In FIG. 3, a through-hole 11 in order that a cotton portion 6a of the cotton swob passes through is opened adjacent to the retrieving cotton swob port 10 on the wall of the cylinder body and toward the cap end of the cylinder body. And, a neck portion 12 is formed between the thorough-hole 11 and the retrieving cotton swob port 10. On a part of the top opening edge of the cylinder portion 1, a recessed portion 13 is formed to form a wall stop 13a in order to limit a predetermined range to the rotation of the shutter portion 2 as will be set forth.

Figure 4:
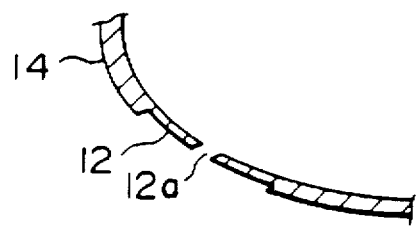
FIG. 4 is a fragmentary sectional view of a recessed portion taken along the IV—IV line in FIG. 3.

The neck portion 12 has an incision without crearance or a slot 12a opened to have a narrower distance than the thickness of a stem 6b of the cotton swob as shown in FIG. 4, in which the slot 12a or the incision communicates between the retrieving cotton swob port 10 and the through-hole for the cotton portion 11. A side surface 14, formed on the circumference face of the cylinder portion and forming thereon with the retrieving cotton swob port 10 and the through-hole for the cotton portion 11 on the retrieving cotton swob port 10, is formed to be slightly thicker than the other outer circumference face 15, between which forms a gap 16 at the border portion. The neck portion 12 is formed to be even thinner than the thickness of the outer circumference face 15, in which the neck portion 12 can be easily bent when the stem of the cotton swob passes through therein. That is, the relationship among the thicknesses of the parts on the circumference side of the cylinder portion is the side surface 14>the outer circumference face 15>and the neck portion 12. The cotton swob 6 can be smoothly retrieved from the container by structuring the neck portion as described above. The material for the cylinder body uses plastic, more preferably, transparent or translucent plastic in order to confirm the accommodated cotton swob from the outside.

When the cotton swob 6 is accommodated in the cylinder body 1, the stem 6a of the cotton swob is retained by the neck portion 12, whereby the cotton swob never protrudes or falls out. In other words, when the stem of the cotton swob is drawn out toward the outside by being held by fingers that enter from the retrieving cotton swob port 10, the neck portion 12 is opened by being pushed by the stem of the cotton swob, and then is returned to its original form by the elastic stability of the neck portion 12, resulting in the prevention of the cotton swob that is accommodated in the container sticking when being removed and returned.

The floor of the cylinder body has two levels, a lower level in the area of the retrieving cotton swob port 10 and a stepped higher level in the area away from the retrieving cotton swob port 10, in which is provided thereon a step 1a between the lower area and the higher area. When the number of cotton swobs are fewer, the step 1a creates a small slant of the cotton swobs to cause the bottom ends (the cotton portions 6b) of the cotton swobs 6 to stand against the step 1a as shown in FIG. 1, with the result that it is easy to take out the cotton swobs.

Figure 5:
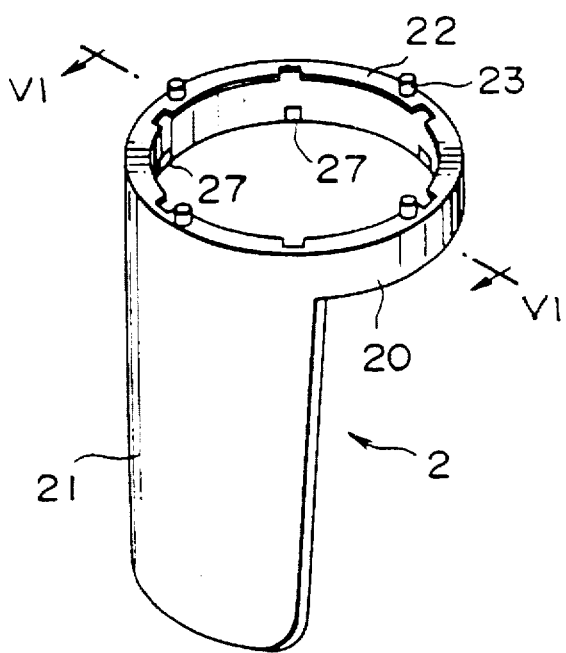
FIG. 5 is a perspective view of a shutter portion.

The shutter portion 2 is composed of an annular ring 20 rotatably supported along the top circumference of the cylinder body 1 and a shutter 21 unitedly formed with the annular ring 20 to open the retrieving cotton swob port 10 of the cylinder body 1. As shown in FIG. 5, a ring-shaped brim portion 22 is formed with the annular ring 20 to extend toward the inside of the cylinder body in order to abut with the top edge opening of the cylinder.

Figure 6:
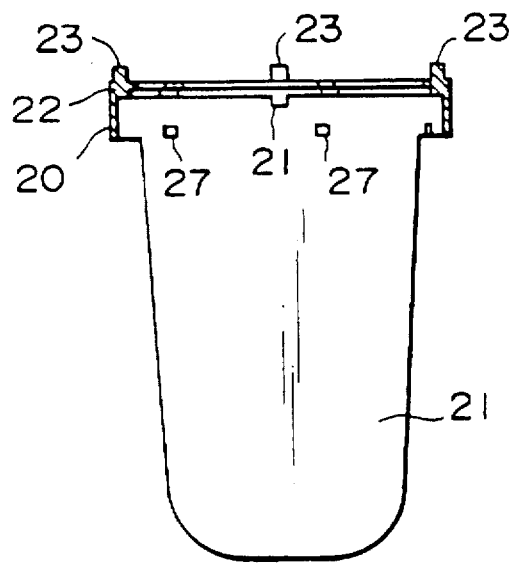
FIG. 6 is a sectional view taken along the VI—VI line in FIG. 5.
Figure 9:
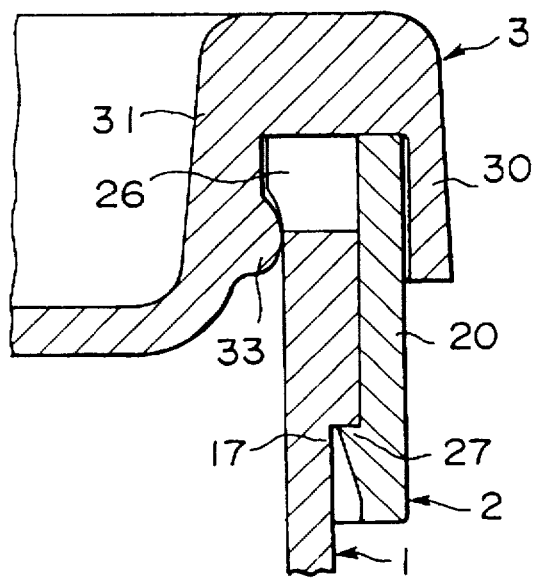
FIG. 9 is a fragmentary sectional view taken along the IX—IX line in FIG. 2.

Plural projecting dowels 23 engaged with the cap 3 are provided on the top face of the brim portion 22. A wall portion 26 projecting toward the inside of the cylinder body (see FIG. 10) is provided at the inside of the brim portion 22 under the projecting dowel 23, in which a ring-shaped fitting face 24 is formed to continue from the wall portion 26 in order to unitedly connect the cap 3 with the shutter portion 2. In FIG. 6, a projecting dowel for limiting rotation 25 is unitedly provided under a part of the fitting face 24. The projecting dowel for limiting rotation 25 is provided to correspond with the recessed portion 13 provided on the upper edge opening of the cylinder body 1, in which causes rotation of the shutter 21 to limit by a manoeuvring function with the wall stop 13a. Plural retaining keys 27 are provided on the inside of the annular ring 20 to be engaged by stepping engagement portions 17 formed on the upper outer face of the cylinder body 1 shown in FIG. 9.

When the shutter portion 2 is provided with the cylinder body 1, the annular ring 20 is inserted to the upper portion of the cylinder body to fit the projecting dowel for limiting rotation 25 formed in the shutter portion 2 into the recessed portion 13 of the cylinder body 1, and then the retaining keys 27 are engaged with the stepping engagement portions 17 while the upper portion of the cylinder body 1 is being deformed. At this moment, the brim portion 22 is abutted to the upper edge opening of the cylinder body 1, therefore, the annular ring 20 is rotatably assembled along the outer upper circumference face of the cylinder body 1. Consequently, the shutter 21 can move in a range from an opening position for the retrieving cotton swob port 10 to a closing position for the retrieving cotton swob port 10.

Figure 7:
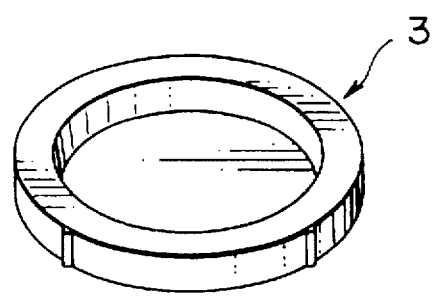
FIG. 7 is a perspective view of a cap.
Figure 10:
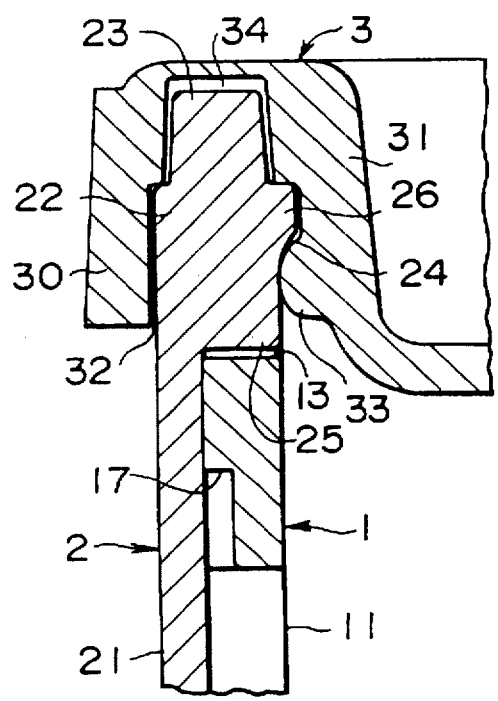
FIG. 10 is a fragmentary sectional view taken along the X—X line in FIG. 2.

The cap 3 shown in FIG. 7 is integrated with the shutter portion to close the opening top of the cylinder body 1 after the shutter portion 2 is assembled with the cylinder body 1. FIG. 10 shows a fragmentary sectional view of the assembly of the container, in which the circumference of the cap 3 is a double-wall structure brought about by an outer circumference wall 30 and an inner circumference wall 31 to have an insert portion 32 inserted with the annular ring 20 forming the brim portion in the shutter portion between the outer and inner circumference walls. The inner circumference wall 31 is provided therein with a ring-shaped engaging portion 33 to engage with the fitting face 24 formed in the brim portion. A receiving recess area 34 is formed on the bottom face of the insert portion 32 to be inserted with the projecting dowel 23 of the shutter portion. After the insert portion 32 formed in the cap is fitted to the annular ring 20 of the shutter portion, the cap 3 is pushed on the top face during the rotation of the cap so as to cause the engaging portion 33 to engage with the fitting face 24 by climbing over the wall portion 26, and at the same time, the projecting dowel 23 is inserted to the receiving recess area 34, with the result that the cap 3 is joined with the shutter portion 2. For turning the cap 3, the shutter portion 2 is rotated, whereby the retrieving cotton swob port 10 can be opened by the shutter 21.

Figure 8:
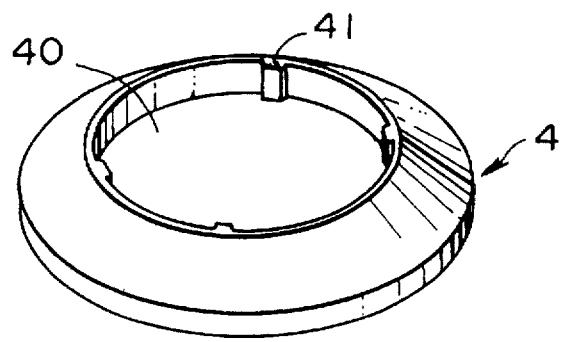
FIG. 8 is a perspective view of a pedestal.

The pedestal 4 shown in FIG. 8 is detachably provided with the cylinder body 1, in which it is structured that the cylinder body 1 can be removed from the pedestal 4 to be easily carried and be attached onto the pedestal 4 when being used for the purpose of being placed on a stable surface in, for example, a person's house. A cylinder receiver 40 is provided in the pedestal 4 to be inserted with the lower portion of the cylinder body 1, and a cylinder engagement portion 41 is provided on a side wall of the cylinder receiver 40 to project toward the inside of the cylinder receiver 40. On the other hand, an engaging hole 18 is opened on the lower portion of the cylinder body 1 to be engaged with the cylinder engagement portion 41 formed in he pedestal 4. When the cylinder body 1 is attached onto the pedestal 4, the lower portion of the cylinder body 4 is elastically deformed to be able to insert into the cylinder receiver of the pedestal, and then the cylinder engagement portion 41 is inserted into the engaging hole 18.

Figure 11:
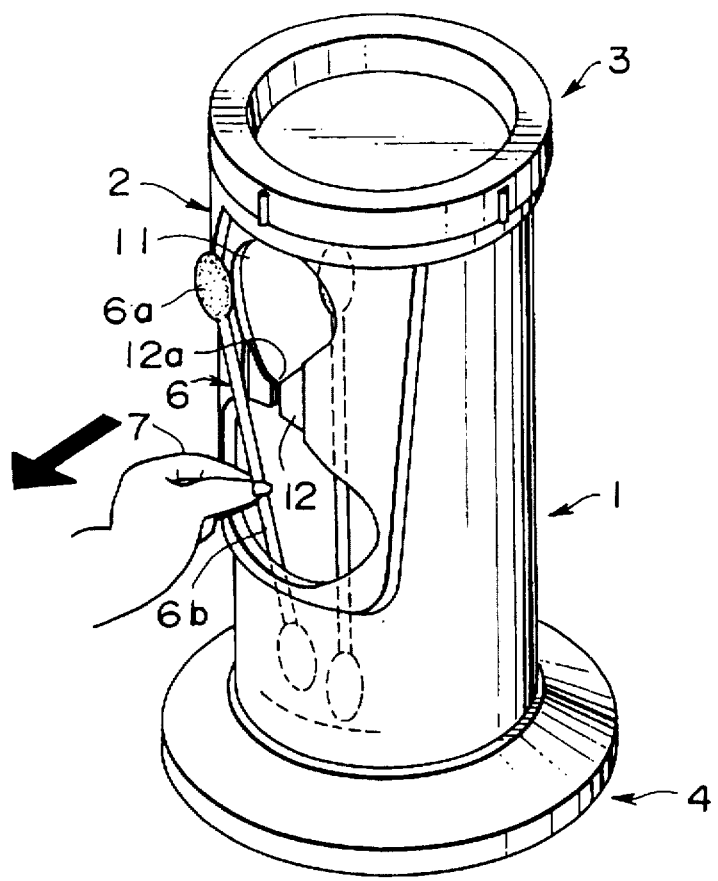
FIG. 11 is an explanatory view of the cotton swob container when it is used.

The following will be explained as to a method for using the cotton swob container based on the first embodiment. FIG. 11 shows when the cotton swob is taken out from the container. When using the cotton swob, it is necessary to turn the cap 3 shown in FIG. 2 clockwise, the shutter 21 is moved and the retrieving cotton swob port 10 is opened as can be seen from FIG. 11. Fingers 7 hold the stem 6b of the cotton swob 6 which is seen from the retrieving cotton swob port 10 and pull out the stem 6a of the cotton swob 6 in an arrow direction to correspond to the through-hole for cotton portion 11. When the stem 6a of the cotton swob 6 passes through the narrow slot 12a of the neck portion 12, the cotton swob can be taken out from the container by forcibly opening the neck portion 12. After the cotton swob is taken out, the cap 3 is turned to move to the original position in the opposite direction when being opened and the shutter 21 closes the retrieving cotton swob port.

Figure 12:
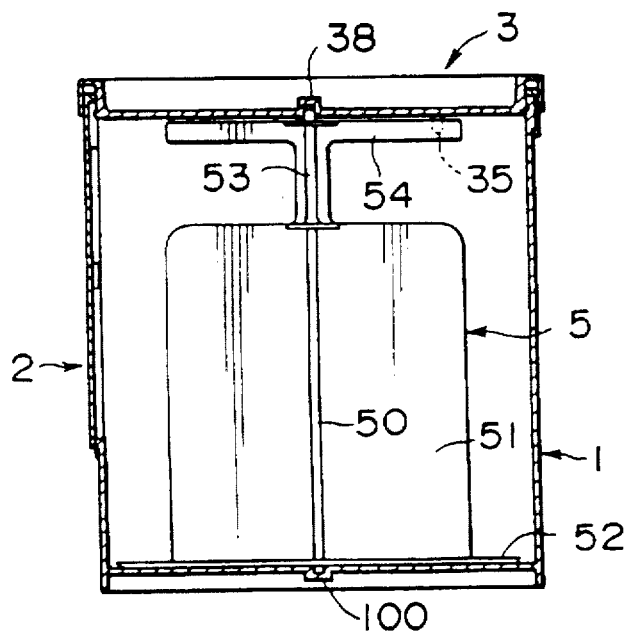
FIG. 12 is a sectional view of a cotton swob container of a second embodiment according to the present invention.
Figure 13:
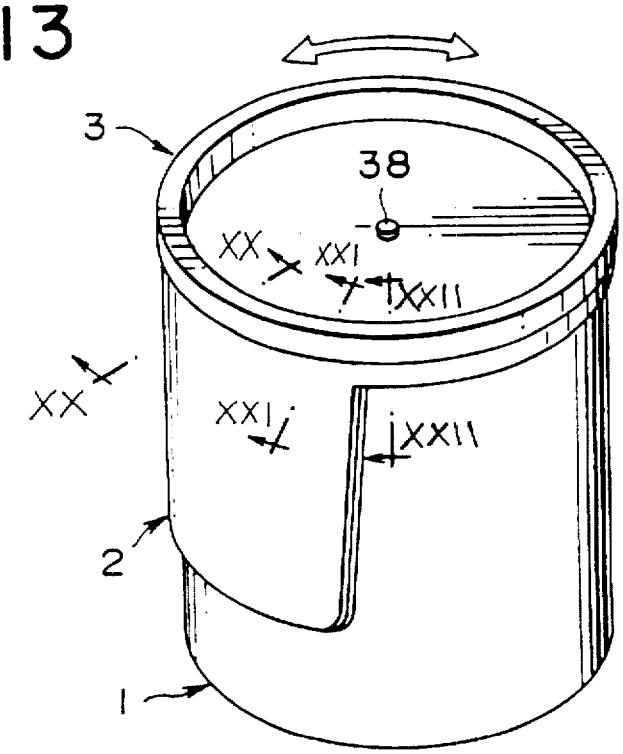
FIG. 13 is a perspective view of the cotton swob container of the second embodiment.
Figure 14:
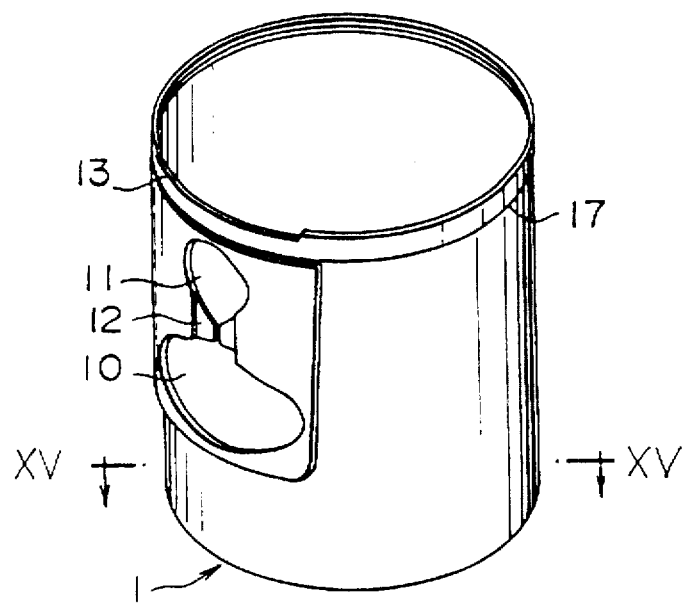
FIG. 14 is a perspective view of a cylinder body of the cotton swob container according to the second embodiment.

FIG. 12 shows a structure of the cotton swob container of a second embodiment according to the present invention, in which the shutter portion is rotatably provided with the cylinder body, and the cap, operating the shutter portion, is detachably connected to the cylinder body. The second embodiment is facilitated so that a divider is provided in order to divide the inside of the cylinder body into plural rooms, in which the container can be used to cause the one divided room to face the retrieving cotton swob port by rotating the divider by operating the cap. Incidentally, in order to avoid overlaping explanations; in the description of the following embodiment, the same reference numerals will be used to designate components having the same or similar functions as those in the first embodiment, so that the description will be omitted or simplified.

Figure 15:
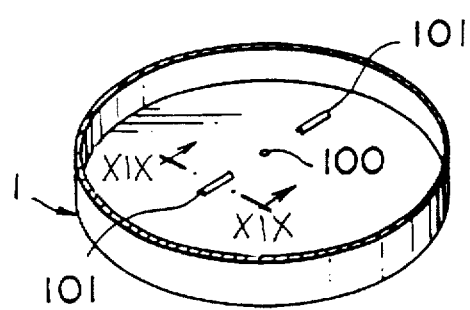
FIG. 15 is a perspective sectional view taken along the XV—XV line in FIG. 14.

The cylinder body 1 according to the second embodiment is basically structured in the same way as the first embodiment, but, the differences between the first and second embodiments are that the container of the second embodiment does not have the pedestal, so that the structure corresponding to the pedestal is omitted, and is characterized by an associated structure with the divider 5 provided in the bottom of the cylinder body. In FIG. 12 and FIG. 15, a lower axle receiver 100 is provided at the center of the floor of the cylinder body 1 to support one end of the axle of the divider 5, and a pair of engagement projecting dowels 101, structuring a set position means for the divider, are formed at symmetrical position about the midpoint for the lower axle receiver 100 to project toward the center of the cylinder body.

Figure 16:
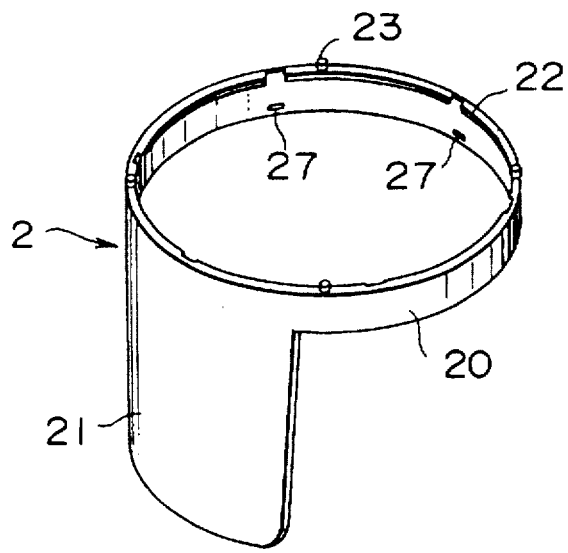
FIG. 16 is a perspective view of a shutter portion applied to the cotton swob container of the second embodiment.

The shutter portion 2 is basically structured in the same way as the first embodiment, however, the one different point is that the shutter portion 2 of the second embodiment does not have a structure for joining with the cap. In FIG. 16, on the top face of the brim portion 22 of the shutter portion 2, the projecting dowels 23 are provided with the corresponding number in response to the number of rooms divided by the divider 5 shown in FIG. 17. The plural retaining keys 27, engaged with the ring-shaped stepping engagement portions 17 formed on the upper circumference face of the cylinder body 1, are provided on the inside face of the annular ring 20.

Figure 18:
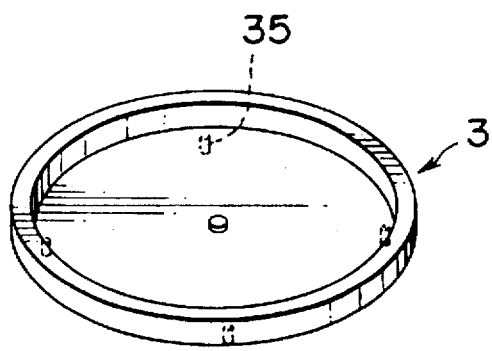
FIG. 18 is a perspective view of a cap portion applied to the cotton swob container of the second embodiment.
Figure 20:
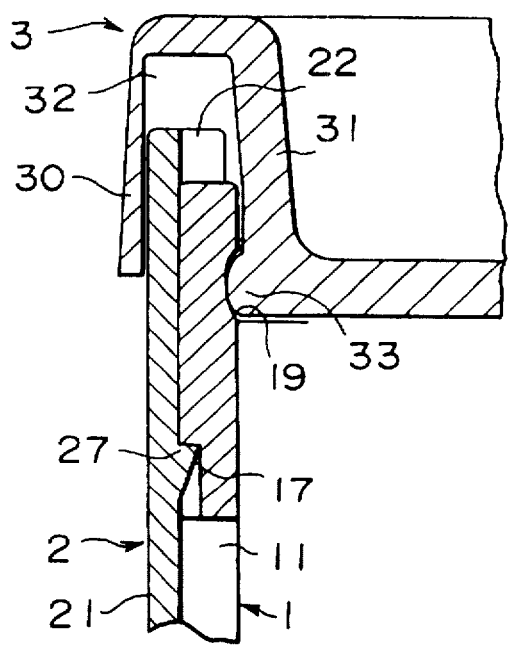
FIG. 20 is a fragmentary sectional view taken along the X—X line in FIG. 13.
Figure 21:
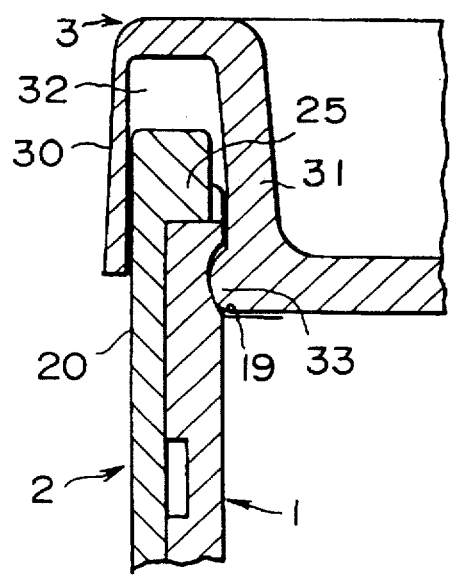
FIG. 21 is a fragmentary sectional view taken along the XXI—XXI line in FIG. 13.

A projecting dowel for rotation operation 35, touching a rotating blade 54 formed with the divider 5, and an upper axle receiver 38, supporting the other end of the axle of the divider 5, are provided on the face of the cap 3 which faces the inside of the cylinder body 1 as shown in FIG. 12 and FIG. 18. The projecting dowel for rotation operation 35 is provided with the coressponding number in response to the number of rooms divided by the divider 5. The engaging portion 33, which is inserted into a ring-shaped groove 19 formed on the inside face in close proximity to the top end of the cylinder body 1 as shown in FIG. 20, is formed on an entrance portion of an inner wall forming the insert portion 32 of the cap.

Figure 22:
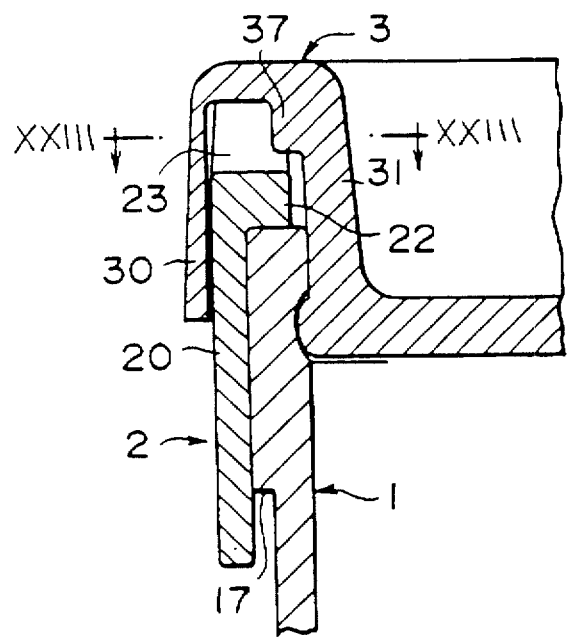
FIG. 22 is a fragmentary sectional view taken along the XXII—XXII line in FIG. 13.

An engaging portion 37, engaging the projecting dowel 23 formed with the shutter portion as shown in FIG. 22, is formed between the inner wall 31 and the bottom face which form the insert portion 32. The number of engaging portions 37 is equal with the number of divided rooms.

Figure 23:
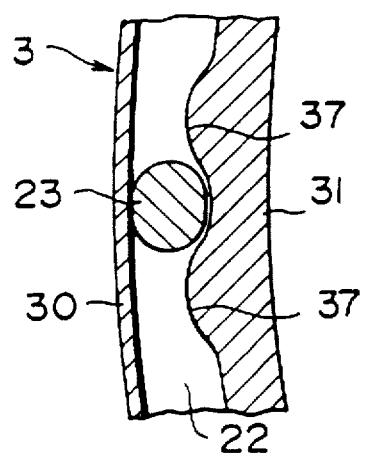
FIG. 23 is a fragmentary sectional view taken along the XXIII—XXIII line in FIG. 22.

FIG. 23 shows when the projecting dowel 23 engages the engaging portion 37. Turning the cap 3, the projecting dowel 23 climbs a hill portion forming the engaging portion 37 to release the mutual engagement, and then is engaged with the next engaging portion 37.

Figure 17:
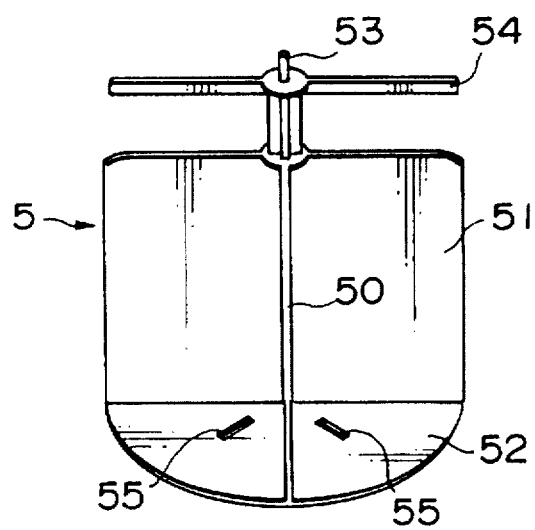
FIG. 17 is a perspective view of a divider.
Figure 19:
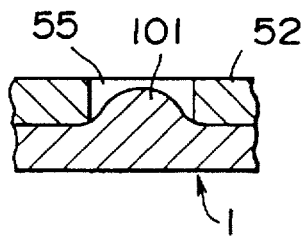
FIG. 19 is a sectional view taken along the XIX—XIX line in FIG. 15.

The divider 5 has plate partitions 50 and 51 mutually crossed at the rotating center as shown in FIG. 17, in which the height of the plate partition is slightly shorter than the length of the cotton swob. Further, a cotton swob receiving plate 52, having smaller interior diameter than the interior diameter of the cylinder body, is unitedly formed with the divider to place on the floor of the cylinder body 1. On the cotton swob receiving plates 52 in response to the divided rooms, an engaging hole 55 is opened to be engaged with the engagement projecting dowel 101 as the set position means in order that the divider 5 is not facilitated to freely rotate when unexpected external forces are acted thereto. FIG. 19 shows the engaging state of the engagement projecting dowel 101 of the cylinder body 1 and the engaging hole 55, namely, the state of the divider 5 set at its position.

The cotton swob receiving plate 52 is formed in order that the lower cotton portion of the cotton swob is not soiled by being rubbed on the floor of the cylinder body 1 when the shutter portion 2 repeatedly opens the retrieving cotton swob port.

One end of a rotating axle 53 of the divider 5 is supported by the upper axle receiver 38 formed to the cap 3, and the other end is supported by the lower axle receiver 100 formed on the floor of the cylinder body 1. The axle—toward the cap, is formed with the rotation blade 54, made with flexibility, touching the side of the projecting dowel for rotation operation 35.

The rotation blade 54 is placed in parallel to one of the plate partitions as shown in FIG. 17 and is provided to touch near its approximate end with the projecting dowel for rotation operation 35.

In the second embodiment, the inside of the cylinder body 1 is divided into the four rooms by the mutually orthogonal plate partitions 50 and 51, however, the number of divided rooms is arbitrarily selected for two rooms, three rooms or the like by means of the structure of the plate partition. And further, a structure without providing the divider 5 is employed.

The following will be explained as to the assembly of the cotton swob container according to the second embodiment.

The divider 5 is put into the cylinder body 1, and a position where the set position means acts is defined. The annular ring 20 of the shutter portion 2 is inserted into the upper portion of the cylinder body to cause the shutter 21 to correspond to the retrieving cotton swob port 10 of the cylinder body 1, and the retaining key 27 formed in the annular ring 20 is engaged with the stepping engagement portion 17 of the cylinder body 1. The insert portion 32 of the cap 3 is inserted onto the annular ring 20 of the shutter portion 2, and then pressed from the upside while being turned. At the same time, the upper axle of the divider is supported by the upper axle receiver of the cap.

The following will be explained about the use of the aforementioned cotton swob container. When the cotton swob is accommodated in each room divided by the plate partition, one of the rooms is faced with the retrieving cotton swob port, and retrieval of the cotton swob is operated by opening the shutter. In the rotation of the cap by the usual operating force, the shutter is moved in a range from a point whereby the shutter portion becomes rotated by engaging the projecting dowel 23 of the shutter portion and the engaging portion 37 to a point where the shutter portion is stopped when touching the projecting dowel for limiting rotation 25 with the wall stop 13a. That is, the retrieving cotton swob port is opened when the cap is at a stopping point on the right rotation so as to be possible to take out the cotton swob, and the retrieving cotton swob port is closed when the cap is at a stopping point on the left rotation.

Using up the cotton swob accommodated in one room, when the cap is rotated by a stronger operating force than usual, the shutter portion is rotated no further after the projecting dowel for rotating limit 25 touches the wall stop 13a, but by forcibly rotating the cap further, the cap is released from its engagement with the shutter portion and can be solely rotated. By the sole rotation of the cap, the projecting dowel for rotation operation 35 of the cap pushes the rotation blade 54, so that the set position of the divider 5 is released through the rotation blade 54 and the divider 5 is rotated. The engaging portion 37 of the cap is engaged with the projecting dowel 23 of the shutter portion, and at the same time, the divider is engaged with the cylinder body so as to be set in its position. Therefore, the next room is placed to face with the retrieving cotton swob port. Since change of the rooms is operated at whether the shutter portion is in a position of closing or opening, the projecting dowel for rotation operation 35 of the cap becomes distant from the rotation lever 54 of the divider which has pushed the projecting dowel 35 thus far by the turning operation for the cap in the opposite direction. Therefore, a retrieval of the cotton swob accommodated in the new room can be operated as usual.

Figure 24:
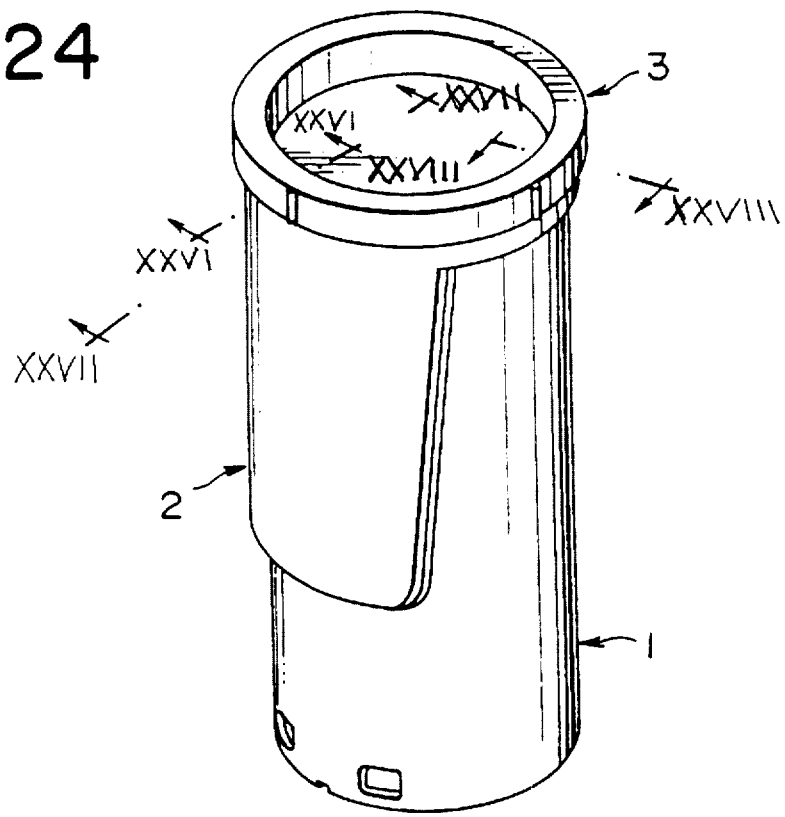
FIG. 24 is a perspective view of a cotton swob container of a third embodiment according to the present invention.

FIG. 24 shows a visual structure of the cotton swob container of a third embodiment according to the present invention. In the third embodiment, the shutter portion is rotatably provided with the cylinder body, and further the cap operating the shutter portion is detachably joined with the cylinder body, in which it is characterized that the annular ring portion of the shutter portion is structured by a double-wall having a sectional U-shape having its opening at the base to be formed with the ring-shaped groove for engaging with the cap on the outer lower side of the inner wall forming the annular ring portion. Incidentally, in order to avoid an overlaping explanations; in the description of the following embodiment, the same reference numerals will be used to designate components having the same or similar functions as those in the first embodiment, so that the description will be omitted or simplified.

Figure 25:
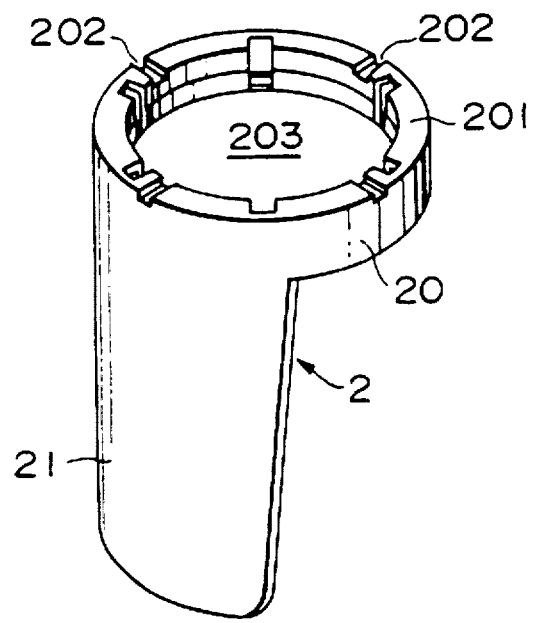
FIG. 25 is a perspective view of a shutter portion applied to the cotton swob container of the third embodiment.

The cylinder body 1 has the same structure as the first embodiment, so that only the shutter portion will be set forth here in detail. In FIG. 25, the shutter portion 2 is rotatably supported along the outer upper circumference of the cylinder body, and further includes the annular ring 20 unitedly formed with the shutter 21 which opens the retrieving cotton swob port 10 formed on the cylinder. On a top face 201 of the annular ring, plural concave portions 202 are formed to engage with the cap 3. Further, on the inside face of the outer wall of the annular ring, plural retaining keys are formed to engage with the cylinder body.

Figure 26:
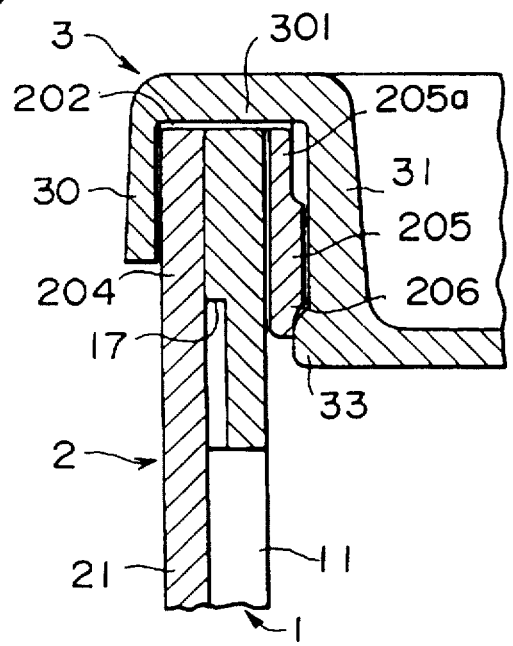
FIG. 26 is a fragmentary sectional view taken along the XXVI—XXVI line in FIG. 25.
Figure 27:
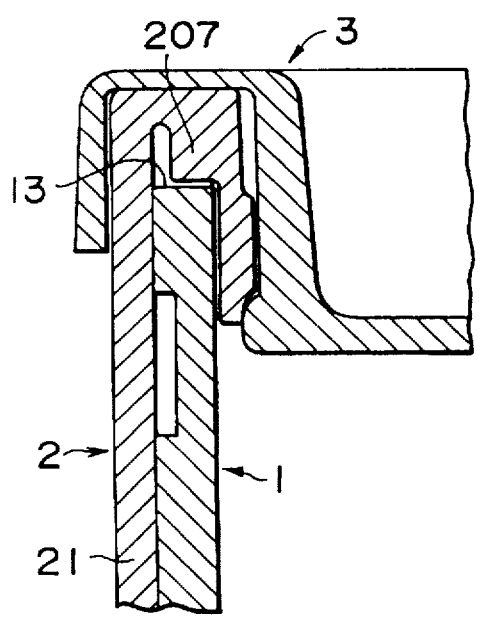
FIG. 27 is a fragmentary sectional view taken along the XXVII—XXVII line in FIG. 24.

The associated structure among the cylinder body, the shutter portion and the cap will be explained in reference to FIG. 26 to FIG. 28. In FIG. 26, the annular ring included in the shutter portion is a sectional U-shape having its opening at the base caused by an outer wall 204 and an inner wall 205, in which a fitting face 206 engaging the engaging portion 33 formed in the cap is formed at the lower end of the inner wall 205. The inner wall 205 has a thin portion 205a formed even thinner on the upper side of the annular ring to wholly impart elasticity. The thin portion 205a is formed to trim to cause the engaging portion 33 of the cap to pass thereon. More preferably, the interior diameter of the annular ring corresponding to the thin portion 205a is formed to be equal to or a slightly larger than the exterior diameter of the cap which corresponds to the engaging portion 33.

Therefore, since the engaging portion 33 of the cap is inserted to be guided with the inside of the thin portion 205a, placement of the cap is to be easy. After the placement of the cap, the correcting force held by the thin portion 205a causes an engaging state between the fitting face and the engaging portion to be ensured more than ever, thereby maintaining the cap in its position.

The concave portion 202 inserted with an engagement projection 301 of the cap is formed on the top face of the annular ring. While, the retaining key 203 (see FIG. 28), which is engaged with the stepping engagement portion 17 formed on the upper outer circumference wall of the cylinder body 1, is formed on the inner circumference face of the outer wall 204. A projecting dowel for rotating limit 207 shown in FIG. 27 is formed on the bottom face of the sectional U-shape having its opening at the base of the inside of the annular ring 20, in which the projecting dowel for rotating limit 207 is placed to correspond to the recessed portion 13 formed in the cylinder body 1 to limit the rotation of the shutter 21.

Figure 28:
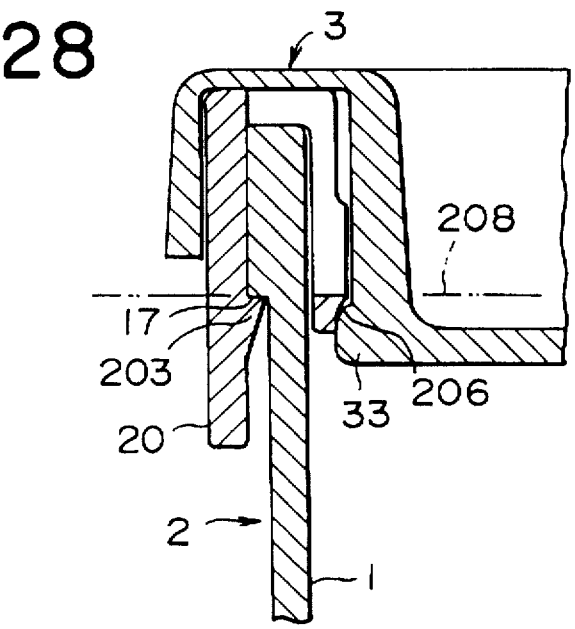
FIG. 28 is a fragmentary sectional view taken along the XXVIII—XXVIII line in FIG. 25.
Figure 29:
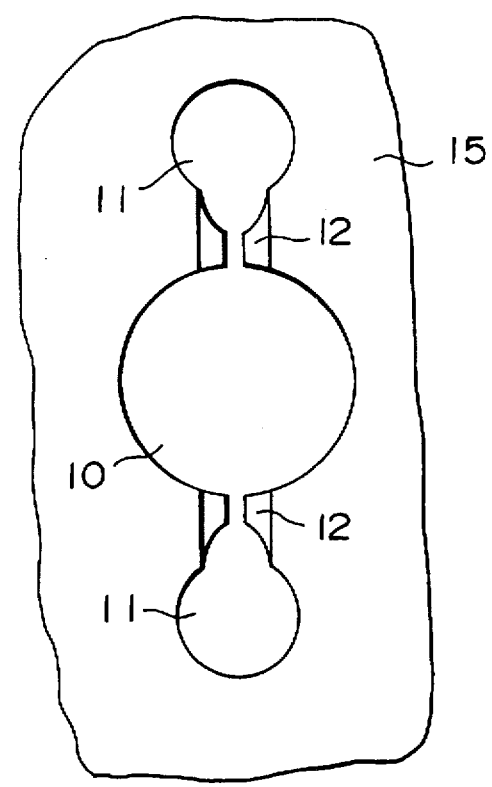
FIG. 29 is a front view of a retrieving port of a rodlike object according to another embodiment.

As shown in FIG. 28, the inner wall of the fitting face 206 is formed to be at approximately the same level as the retaining key formed on the outer wall. Generally, the part of the die used for forming a fitting face having a curvature is easily damaged, resulting in the disadvantage as to the durability of the die, however, by employing the shutter portion structure according to the embodiment, it is possible to assign a molding die at a line 208 shown in the drawing, resulting in an improvement of the durability of the die.

The third embodiment can be naturally applied to the container in which the inside of the cylinder body is divided into plural rooms by the divider.

The present invention is not intended to be limited to the container for the cotton swob which is described in the aforementioned embodiments, and can be applied to the container for accommodating rodlike objects, such as a toothpick, golf tee or the like.

INDUSTRIAL AVAILABILITY

As described thus far, the container according to the present invention is composed of three members: the cylinder body, the shutter portion and the cap, whereby easier production of each part, fewer numbers of parts, and further simplified assembly are possible, resulting in a small cost of production.

The cap is engaged by an engagement means which is formed on the inner face of whether the shutter or the cylinder body, so that the rotating operation of the cap can be smoothly performed for a long time, resulting in the improvement of operability and reliability of the retrieval of the rodlike object.

The neck portion having a smaller clearance than the thickness of the rodlike object is formed between the retrieving port and the through-hole for the head portion, so that only the middle portion of the rodlike object is touched when being retrieved, whereby, for example, when the cotton swob is taken out, there is no apprehension that the cotton portion is polluted or soiled with fingers and the cotton swob is maintained in a hygienic state.

I claim:

1. A container for accommodating elongated objects, each of which has a stem and a head portion, the container comprising:

a cylindrical body having a circumferential wall;

a retrieving area formed on said circumferential wall, said retrieving area including a retrieving port, a through-hole for passing the head portion of an object therethrough, and a neck portion formed between said retrieval port and said through-hole, said neck portion creating a slot which communicates with said retrieving port and said through-hole; and a shutter portion including a shutter attached to an annular ring, said annular ring rotatably supported on said circumferential wall of said cylindrical body for rotation between a first position, wherein said shutter portion closes said retrieving area, and a second position, wherein said retrieving area is open.

2. The container according to claim 1, wherein said neck portion has a first wall thickness and said retrieving area has a second wall thickness, said first thickness being smaller than said second thickness, and wherein said slot is narrower than the stem of said elongated object.

3. The container according to claim 1, wherein said body has an opening, a cap covering said opening, and a divider dividing said body into a number of rooms and relatively connected with said cap, so that said retrieving area corresponds to one room defined by said divider by turning said cap.

4. The container according to claim 1, wherein said body has a divider dividing the inside of said cylinder body into a number of rooms, said divider linked to said shutter portion.

5. The container according to claim 4, wherein said shutter portion has a number of engaging stop means for defining stop positions for said shutter portion.

6. The container according to claim 3 wherein said body includes a floor and said divider has a receiving plate receiving a lower end of said object accommodated in each room divided by said divider to place between said floor of said boy and said divider.

7. The container according to claim 6, wherein said divider and said receiving plate are unitedly formed.

8. The container according to claim 1, wherein said body has a floor, said floor having a lower level on said floor adjacent said retrieving area, a stepped level on said floor away from said retrieving area, and a step between said lower level and said stepped level, said step causing said object to lean toward said retrieving area when said object stands against said step.

9. The container according to claim 1, wherein said container further includes a cap and an open edge, said annular ring includes a thick portion and said body includes an engagement means for engaging with said cap on said thick portion, said shutter portion causing said annular ring to insert into said body to cause said thick portion of said annular ring to abut said open edge of said body to rotate so that said retrieving area is opened by rotating said shutter portion by rotation of said cap.

10. The container according to claim 9, wherein said cap is provided with a fitting means provided on an inner face of said thick portion formed in said annular ring of said shutter portion.

11. The container according to claim 9, wherein said shutter portion has said annular ring formed in a double-wall structure having an inner wall and an outer wall inserted into said body, said annular ring being provided with a fitting means for fitting with said cap on said inner wall of said annular ring placed in said body.

12. The container according to claim 11, wherein said engagement means for engaging with said body is provided on said outer wall of said annular ring separately placed on said body and wherein said fitting means for fitting with said cap is provided on said inner wall of said annular ring, said engagement means and said fitting means being provided on a same level.

13. The container according to claim 4, wherein said body includes a floor and said divider has a receiving plate receiving a lower end of said object accommodated in each room divided by said divider to place between said floor of said cylinder body and said divider.

14. The container according to claim 9, wherein said cap includes an upper inner face, said cap including a fitting means on said inner face for fitting said cap.

* * * * *